(12) United States Patent
Heath et al.

(10) Patent No.: US 7,786,295 B2
(45) Date of Patent: Aug. 31, 2010

(54) METHOD TO ISOLATE DNA

(75) Inventors: Ellen M. Heath, Minnetonka, MN (US); Nathaniel W. Morken, Maple Grove, MN (US); Kristen Campbell Benedict, Maple Grove, MN (US)

(73) Assignee: Qiegen North American Holdings, Inc, Germantown, MD (US)

( * ) Notice: Subject to any disclaimer, the term of this patent is extended or adjusted under 35 U.S.C. 154(b) by 0 days.

(21) Appl. No.: 10/075,593

(22) Filed: Feb. 15, 2002

(65) Prior Publication Data
US 2003/0157492 A1 Aug. 21, 2003

(51) Int. Cl.
*C07H 21/00* (2006.01)
*C12Q 1/68* (2006.01)
*C07H 21/02* (2006.01)

(52) U.S. Cl. .......... 536/25.4; 435/6; 536/23.1
(58) Field of Classification Search ............. 435/6; 536/23.1, 25.4
See application file for complete search history.

(56) References Cited

U.S. PATENT DOCUMENTS

| | | | |
|---|---|---|---|
| 5,010,183 A | | 4/1991 | Macfarlane |
| 5,057,426 A | * | 10/1991 | Henco et al. ............ 435/270 |
| 5,234,809 A | | 8/1993 | Boom et al. |
| 5,393,672 A | | 2/1995 | Ness et al. |
| 5,596,092 A | * | 1/1997 | Schneider ............ 536/25.4 |
| 5,777,098 A | * | 7/1998 | Gray et al. .......... 536/25.41 |
| 5,973,137 A | | 10/1999 | Heath |
| 6,780,632 B1 | * | 8/2004 | Hanak et al. ............ 435/270 |
| 2002/0068280 A1 | * | 6/2002 | Fairman ................ 435/6 |
| 2003/0082616 A1 | * | 5/2003 | Tomita et al. ............ 435/6 |

FOREIGN PATENT DOCUMENTS

WO WO 96/18731 6/1996
WO WO 97/10331 3/1997

OTHER PUBLICATIONS

Heath et al. Use of buccal cells collected in mouthwash as a source of DNA for clinical testing. Arch Pathol Lab Med, vol. 125, 2001.*
Miller et al. A simple salting out procedure for extracting DNA from human nucleated cells. Nucleic Acids Res., vol. 16, No. 3, p. 1215, 1988.*
Younghusband et al. Adenovirus DNA is associated with the nuclear matrix of infected cells. J Virol., Vo. 43, No. 2, pp. 705-713, 1982.*
Moskaitis, J.E. et al., Neurochem. Res., vol. 11, pp. 299-315 (1986).*
Shih, Y-C. et al., Biotechnol. Bioeng., vol. 40, pp. 1155-1164 (1992).*
Coen, C.J. et al., Biotechnol. Bioeng., vol. 53, pp. 567-574 (1997).*
Laitinen, J. et al., Biotechniques, vol. 17, pp. 316, 318, 320-322 (1994).*
Lahiri, D. K. et al., Nucl. acids Res., vol. 19, p. 5444 (1991).*
Ausubel et al., Current Protocols in Molecular Biology, 4.0-4.-4.5.3 and 13.12.1-13.12.3, John Wiley & Sons, NY, 1989.
J. Favaloro et al., Transcription Maps of Polyoma Virus-Specific RNA: Analysis by Two-Dimensional Nuclease S1 Gel Mapping, Methods in Enzymol, 1980, pp. 718-749, vol. 65.
Molecular Cloning: A Laboratory Manual, 2nd ed. 7.3-7.24 Cold Springs Harbor Springs, NY, 1989.

* cited by examiner

*Primary Examiner*—Teresa E Strzelecka
(74) *Attorney, Agent, or Firm*—Baker Donelson Bearman Caldwell & Berkowitz PC

(57) ABSTRACT

An improved method for isolating DNA from biological samples is provided.

38 Claims, No Drawings

METHOD TO ISOLATE DNA

BACKGROUND OF THE INVENTION

As medical science continues to advance, the uses for isolated DNA and the desire for increased quantities of isolated DNA have led to a number of different methods for its isolation. Isolated DNA is employed in numerous applications, including gene discovery, disease diagnostics, drug discovery, the forensic sciences, and other research and clinical applications, including recombinant DNA research, cloning, sequencing, etc., using techniques such as hybridization, amplification, etc. Typically, DNA is isolated from cells in three sequential stages: (1) cells are lysed to release their content which includes protein, lipids, RNA and DNA; (2) ribonucleases (RNases) are optionally added to remove RNA; and (3) non-DNA contaminants such as protein are removed to yield pure DNA.

Methods for isolating nucleic acids from biological samples such as blood, cultured cells, tissues or body fluids typically are initiated by adding the biological sample directly to a detergent-containing lysis solution or a chaotropic-containing lysis solution sometimes also in the presence of a particulate solid phase (e.g., WO 96/18731 (Deggerdahl et al.), U.S. Pat. No. 5,234,809 (Boom et al.)). Alternatively, cells may be concentrated first by centrifugation and the suspended in a suspension solution. Achieving a uniform suspension of the compacted cells improves nucleic acid isolation by allowing more uniform contact with the detergent and/or chaotropic reagents that disrupt cell membranes and structures. Typical suspension solutions are hypotonic, such as that used in a pretreatment step to lysis red blood cells in mammalian blood (U.S. Pat. No. 5,777,098 (Gray), U.S. Pat. No. 5,973,137 (Heath et al.) or isotonic solutions such as phosphate buffered saline (e.g., WO 96/18731 (Deggerdahl et al.)), glucose (WO 97/10331 (Gonzales)) or sorbitol (U.S. Pat. No. 5,973,137 (Heath et al.)).

Several lysing reagents have been formulated to lyse cells. A lysate is created by mixing a biological sample comprising cells or viruses with the lysing reagent, by grinding tissue samples with a pestle in the presence of the lysing reagent thus facilitating penetration of the lysing reagent into the cells, or by dissociating tissue samples through mechanical or other means (for example, using sonication). The lysing reagent typically contains a detergent to disrupt cell membranes and solubilize proteins and lipids. The most common detergents used in lysing reagent formulations are the anionic detergents sodium dodecyl sulfate (SDS) and N-Lauroyl sarcosine as described in Sambrook et al. (*Molecular Cloning: A Laboratory Manual*, $2^{nd}$ ed., 7.3-7.24, Cold Spring Harbor Press, Cold Spring Harbor, N.Y. (1989)) and Ausubel et al. (*Current Protocols in Molecular Biology*, 4.0-4-4.5.3 and 13.12.1-13.12.3, John Wiley & Sons, New York (1989)). Non-ionic and cationic detergents have also been described for this purpose by Favaloro et al. (*Methods Enzymol*, 65, 718-749 (1980)) and U.S. Pat. No. 5,010,183 (MacFarlane) respectively.

After lysis, DNA is generally purified by separating it from the complex lysate, which contains non-DNA cellular material such as RNA, lipids and protein. The lysate is generally mixed with an organic solvent—typically, phenol and/or chloroform. Phenol not only denatures proteins but, following centrifugation, causes the protein to collect at the interface between the organic and aqueous layers; chloroform facilitates the separation of organic and aqueous phases. Such reagents, however, are typically unstable during storage due to oxidation. Moreover, these reagents are hazardous chemicals. Toxicity of such reagents is indicated by their $LD_{50}$ values. The lower the $LD_{50}$ value, the more hazardous the compound. Generally, lysing and/or purification solutions contain chloroform, which is highly toxic and a known carcinogen, having an $LD_{50}$ of 908 mg/kg (rat oral administration). Phenol is highly toxic as well, having an $LD_{50}$ of 317 mg/kg (mouse oral administration). A method for DNA isolation that uses less hazardous compounds, such as benzyl alcohol to replace phenol and chloroform, is disclosed by (U.S. Pat. No. 5,393,672 (Ness et al.)). However, despite the lower toxicity of benzyl alcohol, it is still classified as harmful with an $LD_{50}$ of 1230 mg/kg by rat oral administration. Furthermore, even less toxic organic solvents require special handling and disposal.

Yet another major problem with conventional DNA isolation methods is the extensive labor and time required. The isolation of DNA from biological samples has been and continues to be labor intensive, requiring time consuming and repetitive tasks that occupy the bulk of a technician's time, often to the exclusion of other tasks. Currently, manual processes for the isolation of DNA require a time intensive operation of up to 24 hours. Excluding any incubation period, a technician may be required to perform upward of twenty tasks on a regular basis during the isolation process. The repetitive yet delicate process steps of DNA isolation require precision and attention to detail, and the relative success and/or yield may often rely on the skill of the technician responsible for the isolation. Repetitive application of precise process steps lends itself to errors which may negatively affect the quality and/or quantity of DNA isolated from a sample, or result in contamination of the sample. Furthermore, the generally large number of process steps required to isolate DNA increases the risk for contamination and cross-contamination of samples. In the case of unique or limited samples, such errors may occur when dealing with samples that cannot be duplicated, or are irreplaceable.

There exists a need for a method for the isolation of DNA from biological samples that does not employ harmful toxic reagents, and that employs fewer steps than conventional methods.

SUMMARY OF THE INVENTION

The current invention overcomes the problems of the prior art by providing an improved method for isolating DNA. First, the current invention reduces the number of steps in the process from that observed in standard DNA purification methods and does not involve the use of toxic chemicals while achieving DNA yields and purity that are at least comparable to those observed in conventional DNA isolation methods. Second, the invention teaches the unexpected finding that a reversal of the sequence of steps commonly encountered in the prior act, to isolate DNA results in comparable yields and purity of DNA while, in fact, reducing the overall number of steps and reagents required. The invention achieves these dual goals by first adding a hypertonic, high-salt reagent to biological material containing DNA—for example white blood cells, followed by the sequential addition of a cell lysing reagent, and optionally RNase. Optionally, the biological sample containing DNA may be separated from the remainder of the biological sample. For example, white blood cells containing genomic DNA may be separated from the remainder of a blood sample by selectively separating them from red blood cells and other blood components. The addition of a hypertonic, high-salt reagent before the addition of a lysis reagent facilitates the resuspension of cells such as white blood cells in a single step, improves the availability of the cells for subsequent cell lysis without the additional use of multiple resuspension steps, and obviates the need for the further addition of another protein precipitation reagent after cell lysis, contrary to what is observed in most conventional DNA isolation methods. In the current invention a single post-lysis step of, a single physical means of separation such as centrifugation can conveniently separate the DNA from the non-DNA cellular materials which can often be centrifuged or precipitated while the DNA remains in suspension. Methods of DNA isolation disclosed in the prior art, however, teach the addition of a lysis reagent first, followed by the addition of a protein precipitation reagent and an additional separate physical separation step such as centrifugation to separate the DNA from non-DNA cellular material such as RNA, proteins, lipids, etc. Other methods in the prior art call for post-lysis resuspension processes involving multiple steps. Furthermore, in the methods commonly encountered in the prior art additional post-lysis steps may be needed to break apart clumps or aggregates of cellular material before a protein precipitation reagent is added. Such methods include heating the lysate, physical resuspension and the addition of enzymes such as Proteinase K. The sequence of steps disclosed in the current invention obviate the need for any post lysis methods to prevent clumping because the disclosed sequence of steps prevent such clumping from occurring. In some instances in the prior art additional steps are incorporated into the method prior to the addition of the lysis reagent. For instance, a hypotonic solution may be first added to remove lipids and other contaminants in solution, after which the same hypotonic solution is used in at least one other cell resuspension step. See U.S. Pat. No. 5,777,098 (Gray et al.). This necessitates the additional step of adding yet another reagent, i.e., a protein precipitation reagent after cell lysis. In contrast, the method of the current invention does not require the use of a hypotonic solution to remove lipids and resuspend the cells. The invention of the current method allows the cells to be directly suspended in a hypertonic, high-salt reagent, followed by the addition of a lysis reagent. This convenient, rapid method results in comparable yields and purity seen in the more conventional aforementioned methods of the prior art, with fewer reagents, fewer steps, and subsequently less overall time and effort.

The direct addition of the aforementioned reagents in the sequence described results in a significant saving of time for all relevant processes involving DNA purification, but is especially beneficial when processing multiple samples. For example, processing 8 blood samples using the method of the current invention can be accomplished in 45 minutes or less in contrast to the 120 minutes or more required using more conventional methods. This is accomplished by the use of fewer reagents and/or steps. Furthermore, the direct addition of the hypertonic, high-salt reagent to a concentrated sample of cells, (for example, a centrifuged pellet of white blood cells) causes the cells to go into suspension immediately without the use of additional physical resuspension steps such as vortexing, multiple pipetting, sonication, etc. Furthermore, the addition of the aforementioned reagents in the sequence described results in comparable downstream DNA yields to those obtained using conventional DNA isolation methods. Equivalent yields are obtained even in those samples, which have been stored for a long period of time, that show clotting or are compromised in any manner. Furthermore, the addition of the hypertonic, high-salt reagent to a cell pellet results in reduced levels of RNA contamination than what is normally encountered in methods used by those skilled in the art. This reduced level of RNA contamination eliminates the need for a separate RNA removal step.

In one embodiment of the invention, a method is provided for separating DNA from a biological sample, which comprises cells. The cells can be cultured cells, primary cells, cells in a physiological sample, e.g., a physiological fluid such as blood or a tissue sample. The cells may be from any source including microorganisms, viruses, plants, yeast, fungi, or from an animal source, e.g., vertebrates such as primates, humans, or cells from a canine, bovine, feline, caprine source, etc. The hypertonic, high-salt reagent is added directly to the cells, after which a lysis reagent is added to facilitate cell lysis. The lysis reagent may contain RNase.

DETAILED DESCRIPTION OF THE INVENTION

The present invention provides methods and kits that use aqueous reagents for isolating DNA from biological samples. Such biological samples containing DNA include, but are not limited to: (i) biological materials, in an aqueous mixture that contains DNA or as a dried sample (for example, a dried blood spot); (ii) complex biological mixtures of prokaryotic or eukaryotic cells; (iii) physiological fluids such as blood, saliva, cerebrospinal fluid, etc.; (iv) solid animal tissues such as heart, liver, and brain; (v) animal waste products such as feces and urine; (vi) plant tissues; (vii) yeasts, bacteria, viruses, mycoplasmas, fungi, protozoa, rickettsia; and (viii) other small microbial cells. Typically, the biological material also includes proteins and lipids. As used herein, "isolated" DNA means that the DNA is substantially pure, and not substantially damaged by enzymatic or chemical means by the methods employed in the prior art or in the present invention, which can be readily determined by one of skill in the art using standard techniques. As used herein, "substantially pure" means the absence of significant amounts of contaminating substances such as RNA, lipids and proteins, that could interfere with subsequent analyses or uses. DNA as used herein means total DNA, and thus includes genomic DNA, mitochondrial, and plasmid DNA, etc.

Using the method disclosed herein, DNA of high yield and substantial purity can be obtained that is equivalent to that obtained using other more conventional methods. Preferably, the isolated DNA is substantially pure, which can be determined by the absence of significant amounts of contaminating substances such as RNA, lipids and proteins, that could interfere with subsequent analyses or uses. For example, the isolated DNA may be used in a variety of downstream analytical or diagnostic methods commonly encountered in the art, such as amplification, hybization, sequencing, Southern blotting, polymerase chain reaction ("PCR"), microarray analysis, etc).

The reagents used in the methods and kits of the present invention contain fewer hazardous components than many conventional nucleic acid isolation reagents. Although lower alcohols (i.e., ($C_1$-$C_4$) alkanols) may be used in concentrating DNA and/or removing residual contaminants after cell lysis, reagents of the present invention are substantially free of organic solvents. As used herein, "substantially free" means less than about 1%, and typically less than 0.5%, volume/volume. Generally, the aqueous reagents of the present invention consist of aqueous formulations of common salts and detergents that are stable for at least about three years at room temperature (20-30° C.).

The first reagent, referred to herein as a "hypertonic, high-salt reagent," is a hypertonic reagent that includes a high concentrations of salts such as sodium, ammonium, or potassium salts dissolved in water. A hypertonic solution is a solution having a higher osmotic pressure than that found within a biological entity such as a cell or tissue. It typically has a high concentration of dissolved solute molecules such as salts. An isotonic solution is a solution having the same osmotic pressure as that found within a biological entity such as a cell or tissue. A hypotonic solution, in contrast, is a solution having a lower osmotic pressure than that found within a biological entity such as a cell or tissue. It typically has a low concentration of dissolved solute molecules or no solute molecules. Suitable salts for use in the hypertonic, high-salt reagent of the current invention are those that are soluble in water and are capable of causing proteins to precipitate from solution. Such salts include, but are not limited to, sodium salts such as sodium chloride and sodium acetate, potassium salts such as potassium chloride and potassium acetate and ammonium salts such as ammonium chloride and ammonium acetate, etc.

The salt is present in the hypertonic, high-salt reagent at a high enough concentration effective to precipitate proteins out of a sample such that the proteins do not interfere in any subsequent downstream analysis of DNA. Preferably, the concentration of such salts is greater than about 1.0 M. More preferably, the concentration of such salts is greater than about 2.0 M. A preferred hypotonic, high-salt reagent is PUREGENE® Protein Precipitation Solution (Gentra Systems, Inc., Minneapolis, Minn., Cat. # D-5003, (Sodium Chloride >5 M)). The hypertonic, high-salt reagent also serves to resuspend cells into solution, thus making the cells available for more efficient subsequent lysis. For example, addition of the hypertonic high-salt reagent to a cell pellet causes the cells to be resuspended almost instantaneously without the formation of aggregates or clumps. Furthermore, the use of the hypertonic, high salt reagent obviates the need for a pre-wash solution, such as a hypertonic wash solution to remove lipids and other contaminants from solution.

For the suspension of yeast cells, an alternative cell suspension reagent may be used. This preferred cell suspension reagent has a pH of about 7-8.5, and more preferably, about 7.5-8.0. This cell suspension reagent keeps cells intact while the cell walls are being digested by lytic enzyme. This reagent contains Tris, preferably, at a concentration of about 0.05-0.15 M, and more preferably, at about 0.08-0.12 M, based on the total volume of the reagent. The Cell Suspension Reagent also contains EDTA, preferably, at a concentration of about 0.05-0.15 M, and more preferably, at about 0.08-0.12 M, based on the total volume of the reagent. The preferred molar ratio of Tris to EDTA is about 1:1. This reagent also contains sorbitol, preferably at a concentration of about 0.8-1.0 M, and more preferably, at a concentration of about 0.85-0.95 M, based on the total volume of the reagent. The Cell Suspension Reagent contains deionized water, preferably deionized to the level of purity described above, and further purified by filtration using a filter of about 0.2 μM pore size.

In one embodiment of the invention, the method includes the lysis of biological material such as cells or viruses which is achieved by combining biological material, comprising cells (or viruses), with a lysing reagent containing an anionic detergent to form a lysate. The lysing reagent is added after the aforementioned hypertonic, high-salt reagent is added to the biological material. As used herein, "lysis" refers to the destruction of a cell by rupture of its membranes. A "lysis reagent," generally includes, but is not limited to, an anionic detergent dissolved in a buffer. The reagent is buffered up to a pH of less than about 10, and preferably, less than about 9. Preferably, the pH of the lysis reagent is maintained at less than about 9 using a buffer, such as Tris-[hydroxymethyl] aminomethane-ehtylenediamine acetic acid (Tris) buffer, although a Tris buffer is not a requirement as long as the buffer is capable of providing a pH of less than about 9 in aqueous media. However, any suitable buffer, known to those skilled in the art may be used. Suitable anionic detergents are those that are soluble in water at a level of at least about 0.1% weight/volume, based on the total volume of the reagent, and are capable of lysing cells and/or solubilizing proteins and lipids at this concentration. Such anionic detergents include, but are not limited to, salts (e.g., sodium, potassium, and lithium salts) of dedecyl sulfate. Preferably, the anionic detergent is a dodecyl sulfate salt. Preferably, the concentration of such a dodecyl sulfate salt is greater than 0.1% w/v. This reagent lyses cells and viruses to form a lysate. A preferred lysis reagent is PUREGENE® Cell Lysis Solution (Gentra Systems, Inc., Minneapolis, Minn., Cat. # D-5002; 0.5% SDS, 0.1 M Tris, 0.1 M EDTA).

Another aspect of this invention involves one or more optional, ancillary reagents in addition to the lysis reagent and the hypertonic, high-salt reagent. These ancillary reagents include reagents known to one of skill in the art for nucleic acid purification. The methods of the present invention, however, are not limited to the use of these specific ancillary reagents, as one of skill in the art may use other reagents and/or techniques to achieve the same purpose. Also, each of the lysis reagent and the hypertonic, high-salt reagent can be used with other reagents and/or techniques if desired.

The first ancillary reagent is a red blood cell lysing reagent ("RBC Lysing Reagent") used when the biological material comprises mammalian whole blood. The red blood cell lysing reagent is used to lyse red blood cells and facilitate subsequent isolation of DNA from the white blood cells contained in mammalian whole blood. This reagent is referred to herein as the "RBC lysis reagent" and comprises compounds such as ammonium chloride, sodium bicarbonate, and EDTA in deionized water at concentrations sufficient to lyse red blood cells preferentially over white blood cells. Such concentrations are known to those skilled in the art. In particular, the RBC lysing reagent causes the preferential rupture of the cellular membrane of red blood cells, while having no significant lysing effect on the cellular or nuclear membranes of white blood cells. The RBC lysing reagent is added to mammalian whole blood which causes the red blood cells to lyse, leaving behind substantially intact white blood cells in solution. The white blood cells (and any cell-associated viruses that may be present) are then separated from the red blood cell lysate by centrifugation or any other appropriate method and the red blood cell lysate discarded, after which the hypertonic, high salt reagent is directly added to the white blood cells. Subsequently, a lysis reagent is added to rupture the membrane thus releasing the DNA. A preferred lysis reagent is the PUREGENE® RBC Lysis Solution (Gentra Systems, Inc., Minneapolis, Minn., Cat. # D-5001; 145 mM ammonium chloride, 0.5-2 mM sodium bicarbonate, and 0.75-1.25 mM EDTA). In the current invention, the RBC Lysing reagent is only used to lyse red blood cells. It is not used to resuspend white blood cells or any other biological material before cell lysis.

Other ancillary reagents can include but are not limited to alcohols, e.g., 100% isopropanol to precipitate DNA, 70% ethanol to wash the precipitated DNA, RNases such as RNase A to remove RNA, Proteases such as Proteinanse K to digest proteins, glycogen to facilitate DNA precipitation and recovery, and a DNA hydration reagent. A DNA hydration reagent is used to dissolved the isolated and purified DNA for storage. If stored in the DNA hydration reagent, the isolated DNA can be stored for an indefinite period of time at temperatures of −20 or −80° C. Preferably, a DNA hydration reagent comprises a buffer, e.g., a buffer with 10 mM Tris, and 1 mM EDTA, pH of about 7-8. A preferred DNA hydration reagent is PUREGENE® DNA Hydration Solution (Gentra Systems, Inc., Minneapolis, Minn., Cat. # D-5004; 10 mM Tris, 1 mM EDTA pH 7.0-8.0).

Another aspect of this invention is a kit that includes specific protocols, which in combination with the reagents described herein, may be used for isolating DNA according to the methods of the invention. The kit includes the lysis reagent and the hypertonic, high-salt reagent. Depending on the application, the kit may also include one or more ancillary reagents described herein. The protocols may be scaled up or down depending upon the amount of biological material used, provided the ratio of reagents remains consistent.

A kit for isolating DNA from mammalian blood may contain the RBC lysis reagent, the lysis reagent, the hypertonic, high-salt reagent, optionally a DNA hydration reagent, and instruction means for isolating DNA from samples of whole mammalian blood—preferably volumes of 0.11 to 50 ml, and more preferably volumes of 5 to 10 ml. Using this kit, DNA is preferably isolated in a yield of at least about 100 to 500 μg per 10 ml whole blood, and typically in a range of about 200 to 400 μg of DNA per 10 ml whole blood. However, the yield depends on the white blood cell count, which varies considerably from individual to individual, or between biological samples A kit for isolating DNA from plant and animal solid tissues, cultured plant and animal cells, body fluids such as cerebrospinal fluid, plasma, saliva, semen, serum, synovial fluid, urine, or gram-negative bacteria contains the lysis reagent, the hypertonic, high-salt reagent, a DNA hydration reagent, and instruction means for isolating DNA from, for example, 50 mg to 2 g plant and animal solid tissue samples, and 1 to 400 million cultured plant and animal cells, 1 to 50 ml body fluids, 1 to 50 ml gram-negative bacteria culture. Using this kit, DNA is preferably isolated in a yield of at least about 1 μg per 1 mg plant or animal solid tissue; at least about 1 to 10 μg DNA per million cells per million cultured plant and animal cells; and at least about 10 to 100 μg per ml overnight culture of gram-negative bacteria.

In some DNA isolation methods disclosed in the prior art, the biological sample is first treated with a reagent that causes lysis of the RBCs. The mixture containing the biological sample and the RBC Lysis reagent is then centrifuged, the red blood cell debris removed, the resulting pellet of white blood cells subsequently washed in a buffer or hypotonic solution, centrifuged again, resuspended in a buffer or hypotonic solution, and then treated with a lysis reagent that causes the cells to lyse. Following this step, a solution of RNase is optionally added to the cell lysate to digest contaminating RNA. Next, a reagent or reagents that promote protein precipitation is added, and the resulting solution is typically centrifuged to collect proteins and other contaminants. The DNA containing fraction is then added to an alcohol such as isopropanol to precipitate the DNA, which is subsequently collected following centrifugation and washed with ethanol.

The methods of DNA isolation disclosed in the prior art employ a lysis reagent before the addition of a protein precipitation step. However, the current invention discloses a novel method in which a hypertonic, high-salt reagent is added first, followed by the addition of a lysis reagent. The hypertonic, high-salt reagent unexpectedly causes the white blood cells to resuspend in solution without the commonly encountered problems of aggregation or clumping. Thus, the hypertonic, high-salt reagent is used to resuspend the material as well as precipitate protein contaminants, which is its normal function. The hypertonic, high-salt reagent in this procedure thus serves three purposes 1) to resuspend the biological material, eliminate aggregation and clumping, and thus facilitate efficient cell lysis; 2) to reduce RNA contamination; and 3) to remove contaminants (for example, proteins) in the presence of detergent, which is its normal function.

The lysis reagent is added after suspending the cells or biological material in the hypertonic, high-salt reagent. Furthermore, in the some embodiments of the invention a lysis reagent to which RNase has been added may also be used. These improvements over prior methods of DNA isolation reduce the number of steps, and thus the time needed for DNA isolation. At the same time, the yields of DNA are comparable to those obtained by standard methods which entailed a greater number of steps and significantly more time and effort. Unexpectedly, no significant RNA contamination is observed in the new and improved method of the instant invention.

Thus, in one embodiment, the methods of the present invention involve combining a biological sample with a hypertonic, high-salt reagent and sequentially contacting it with a lysis reagent to form a lysate containing DNA, then separating the DNA from non-DNA cellular contaminants such as protein and RNA. The lysing reagent may optionally contain an RNase such as RNase A, especially when used on biological material having high levels of RNA. The separation can include precipitation of proteins from the lysate. The DNA supernatant is collected and the DNA precipitated by the addition of a lower alcohol (e.g. 100% isopropanol). The precipitated DNA is then recovered by centrifugation and the supernatant fraction is decanted. The collected DNA pellet is generally washed with 70% ethanol and dried. The DNA is then typically rehydrated with the DNA hydration reagent.

The invention will be further described by reference to the following detailed example. This example is offered to further illustrate the various specific and illustrative embodiments and techniques. All of the raw materials mentioned below are readily available from commercial sources such as Sigma Chemical Company (St. Louis, Mo.), or Gentra Systems, Inc. (Minneapolis, Minn.). The examples below provide detailed descriptions of the standard methods currently employed, the improved method of the invention, and a comparison of both methods

EXAMPLE 1

Comparison of Standard Method to New Rapid Method

Experimental Set Up

A blood sample collected in a standard blood collection bag was obtained from the Memorial Blood Centers of Minnesota and stored at 4° C. until use. DNA was purified from the blood samples within 96 hours of being drawn. DNA was purified using the PUREGENE® DNA Purification Kit (Cat No. D-50K, Gentra Systems, Inc., Minneapolis, Minn.) using both the standard 10 ml whole blood protocol and the new rapid purification protocol. This kit contained the following PUREGENE® reagents: RBC Lysing Solution, Cell Lysis Solution, Protein Purification Solution, RNase A Solution, and DNA Hydration Solution. Additional reagents were also required for the procedure: 100% isopropanol (2-propanol) and 70% ethanol. Note that although the biological material described in this example is a white cell pellet from whole blood, this method is applicable to collected or pelleted cultured cells, virus particles, pellets from solid or liquid body fluids in a saline or detergent solution.

Standard Method for DNA Purification

A volume of 10 ml whole human blood was added to 30 ml RBC Lysis Solution (Gentra Systems, Inc., Minneapolis, Minn.) in a 50 ml centrifuge tube to lyse the red blood cells, which do not contain genomic DNA. Each sample was inverted to mix the contents, and incubated for 10 minutes at room temperature with one additional inversion half way through the incubation period. To collect the white blood cells, which contain genomic DNA, each sample was centrifuged for 10 minutes at 2000×g. The supernatant fraction was removed, leaving behind a visible white cell pellet and about 200-400 µl of residual liquid. Each tube was vortexed vigorously for 10-20 seconds to resuspend the white cells in the residual liquid. To lyse the suspended white cells and release the DNA, a volume of 10 ml Cell Lysis Solution (Gentra Systems, Inc., Minneapolis, Minn.) was added, resulting in a viscous lysate. Each sample was then pipetted up and down a least 3 times to continue lysing the cells and to mix the viscous cell lysate. If cell clumps or aggregates are still visible, the lysate is incubated at room temperature or 37° C. until the lysate appears homogeneous. A volume of 50 µl RNase A Solution was then added to the cell lysate. Each sample was mixed by inverting the tube 25 times, and then incubated at 37° C. for 15 minutes to digest contaminating RNA. To precipitate proteins and other contaminants, 3.33 ml Protein Precipitation Solution (Gentra Systems, Inc., Minneapolis, Minn.) were added to the sample which had been allowed to cool to room temperature. Each sample was vortexed vigorously at the high speed setting for 20 seconds to mix the Protein Precipitation Solution (Gentra Systems, Inc., Minneapolis, Minn.) uniformly with the cell lysate. Each sample was centrifuged at 2,000×g for 10 minutes to collect the precipitated proteins and other contaminants, which formed a tight dark brown pellet. The supernatant fraction, containing the DNA, was poured into a clean 50 ml tube containing 10 ml 100% isopropanol (2-propanol), leaving behind the pelleted contaminants. To precipitate the DNA, each sample was mixed by inverting gently 50 times until visible white threads of DNA formed. Each sample was centrifuged at 2000×g for 3 minutes to collect the precipitated DNA, which was visible as a white pellet. The supernatant fraction was poured off and the tube was drained for several seconds on clean absorbent paper. To wash the DNA sample, a volume of 10 ml 70% Ethanol was added to the DNA pellet and the tube inverted several times. Each DNA sample was centrifuged at 2,000×g for 1 minute to reposition the pellet in the base of the tube so that the Ethanol could be poured off. Each tube was inverted to drain on clean absorbent paper and allowed to air dry for 10-15 minutes. A volume of 1 ml DNA Hydration Solution (Gentra Systems, Inc., Minneapolis, Minn.) was added to the sample and DNA was rehydrated by incubating at room temperature on a rotator overnight (Clay Adams Nutator®, Fisher Scientific Catalog No. 14-062).

Rapid Method for DNA Purification

A volume of 10 ml whole human blood was added to 30 ml RBC Lysis Solution (Gentra Systems, Inc., Minneapolis Minn.) in a 50 ml centrifuge tube. Each sample was inverted to mix and incubated 5 minutes at room temperature with one additional inversion half way through the incubation period. To collect the white blood cells, which contain genomic DNA, each sample was centrifuged for 2 minutes at 2,000×g. The supernatant fraction was removed by decanting, leaving behind a visible white cell pellet and about 200 µl of the residual liquid should remain. White blood cell pellets are generally very difficult to resuspend in solution. Often vigorous stirring, mechanical agitation or resuspension in a PBS buffer or equivalent fails to resuspend the cells adequately, and the cells continue to clump or aggregate. Thus, to resuspend the white cells, 3.33 ml of a hypertonic, high-salt reagent was used PUREGENE® Protein Precipitation Solution (Gentra Systems, Inc., Minneapolis, Minn., Cat. # D-5003, (Sodium Chloride >5 M)) was dispensed vigorously into the center of the white cell pellets to at disperse the white blood cell pellet. Unexpectedly, this forced the white blood cells to form a suspension immediately without any significant damage to the cells (as seen when analyzed under a microscope), and without any further physical dispersion steps. Immediately following this step, a volume of 10 ml cell lysis solution (Gentra Systems, Inc., Minneapolis, Minn.) containing RNase A Solution was added to the sample to lyse the cells. RNase A solution is not required, but was used to provide a more direct comparison with the standard method. To prepare the combined cell lysis solution and RNase A solution, 5 ml of RNase A solution was added to 1000 ml of Cell Lysis Solution and mixed thoroughly prior to starting the procedure; this solution is stable for at least 6 months at room temperature. To mix the reagents with the resuspended cells and to complete cell lysis, each tube was vortexed vigorously for 20 seconds. Then each sample was centrifuged at 2000×g for 2 minutes to collect the precipitated and other contaminants, which formed a tight dark brown pellet.

The supernatant fraction, containing the DNA, was poured into a clean 50 ml tube containing 10 ml 100% isopropanol (2-propanol), leaving behind the pelleted contaminants. To precipitate the DNA, each sample was mixed by inverting gently 50 times until visible white threads of DNA formed. Each sample was centrifuged at 2000×g for 2 minutes to collect the precipitated DNA, which was visible as a white pellet. The supernatant fraction was poured off and the tube was drained for several seconds on clean absorbent paper. To wash the DNA sample, a volume of 10 ml 70% Ethanol was added to the DNA pellet and the tube inverted several times. Each DNA sample was centrifuged at 2000×g for 1 minute to reposition the pellet in the base of the tube so that the Ethanol could be poured off. Each tube was inverted to drain on clean absorbent paper and allowed to air dry for 1 minute. A volume of 1 ml DNA Hydration Solution was added to the sample and DNA was rehydrated by incubating at room temperature on a rotator overnight (Clay Adams Nutator®, Fisher Scientific Catalog No. 14-062).

The volumes of reagents used for this method are generally recommended for sample sizes between 5.1-10.0 ml. However, for sample volumes of about 1.0-5.0 ml, the volumes of reagents mentioned above are halved. The reagent volumes used for such sample sizes are:

| Reagent | Volume for 1-5 ml blood | Volume for 5-10 ml blood |
| --- | --- | --- |
| RBC Lysis Reagent: | 15-19 ml | 30-35 ml |
| Final Blood + RBC Lysis Reagent | 20 ml | 40 ml |
| Hypertonic, high-salt reagent: | 1.67 ml | 3.3 ml |
| Lysis reagent: | 5 ml | 10 ml |
| 100% Isopropanol: | 5 ml | 10 ml |
| 70% ethanol: | 5 ml | 10 ml |
| DNA hydration reagent: | 0.5 ml | 1 ml |

(DNA hydration reagent can be varied to adjust concentration required)

UV Absorbance Determination

DNA yields were determined using a Beckman DU-64 UV spectrophotometer (Fullerton, Calif.). A 10 µl volume of each DNA sample was diluted in 190 µl ultrapure deionized water and mixed by vortexing at high speed for 5 seconds. To obtain the DNA concentration, the absorbance at 320 nm ($A_{320}$ (background)) was subtracted from the reading at an absorbance of 260 nm ($A_{260}$), and the resulting value was multiplied by the DNA extinction coefficient of 50 μg/ml. Then, DNA yield was calculated by multiplying each concentration by the respective DNA volume as estimated by weight in grams. The $A_{260/A280}$ ratio, which estimates protein contamination, was determined by subtracting the background ($A_{320}$) reading from each of the two absorbance readings before they were divided.

DNA Restriction Enzyme Digestion

DNA quality was evaluated further by analyzing digestion with Hind III (New England Biolabs, Beverly, Mass. and Sigma, St. Louis, Mo.) restriction endonuclease. In a digest volume of 25 μl, 2 units of Hind III were added to 1 μg DNA and allowed to digest for 30 minutes at 37° C. To examine the samples for digestion, a volume of 10 μl was analyzed by 0.7% agarose gel containing ethidium bromide at 0.125 μg/ml. The gel was photographed on a UV transilluminator using a Kodak Digital Imaging System EDAS 120 LE (Rochester, N.Y.).

DNA Size Analysis

To estimate DNA size, a sample of 100 ng was loaded into each lane and separated by 0.6% agarose gel electrophoresis. The DNA was electrophoresed for 16 hours at 15 volts using 0.125 mg/mL ethidium bromide in the gel and running buffer. The gel was photographed on a UV transilluminator using a Kodak Digital Imaging System EDAS 120 LE (Rochester, N.Y.). The migration distance of each DNA sample was compared to a 50 kb size reference standard: 100 ng undigested Lambda DNA. High molecular weight DNA, a measure of DNA quality, was estimated as greater than 95% of the DNA being at least 50 kb in size.

DNA Amplification

Purified DNA was evaluated for amplification performance using primers specific to a 1.5 kb target in one of the cytochrome P450 genes (CYP2D6 locus). For each reaction, a quantity of 100 ng DNA was amplified in a 25 μL volume containing: 1X Taq Polymerase Buffer, 0.05 U/μL Taq Polymerase, 1.5 mM $MgCl_2$, and 0.2 mM each dNTP (Promega, Madison, Wis.) as well as forward and reverse primers at 1 μM (Research Genetics, Huntsville, Ala.). The amplification conditions for the CYP2D6 target were: 30 cycles: 94° C. for 30 seconds, 63° C. for 30 seconds, and 72° C. for 30 seconds; 72° C. hold for 6 minutes, 4° C. hold. A volume of 10 μL from each reaction was analyzed by 2% agarose gel electrophoresis.

Results

| Test | Standard Method | Rapid Method | Result |
|---|---|---|---|
| DNA Yield (μg) +/− Std. Dev. (n = 8) | 352 +/− 20 | 332 +/− 10 | Equivalent |
| $A_{260/280}$ (n = 8) | 1.84 +/− 0.01 | 1.83 +/− 0.01 | Equivalent |
| DNA Size (n = 8) | 8/8 >50 kb | 8/8 >50 kb | Equivalent |
| Restriction Enzyme Digestion (n = 8) | 8/8 Digested with Hind III | Digested with Hind III | Equivalent |
| PCR Amplification (n = 8) | 8/8 amplified 1.5 kb CYP2D6 Locus | 8/8 amplified 1.5 kb CYP2D6 Locus | Equivalent |
| Total Time (n = 8) | 117 | 45 | |
| Hands On Time (n = 8) | 49 | 32 | |
| No. Uncapping/Recapping Steps | 8 | 6 | |
| No. Reagent Additions | 7 | 6 | |

Replicate blood samples were used to compare the standard and the rapid methods, using 8 replicates for each method. By reversing the order of addition of the cell lysis solution and the high concentration salt solution in the rapid method, reductions in time and complexity were achieved. These improvements were also enhanced by combining the RNase with the cell lysis solution directly before adding it to the cell pellet. However, when the DNA was analyzed for yield, quality, size, restriction enzyme digestion ability and PCR amplification performance the two methods were equivalent.

What is claimed is:

1. A method for isolating DNA from a biological sample comprising animal cells comprising the following sequential steps:
   (a) separating the cells comprising DNA from the remainder of the biological sample;
   (b) contacting the separated cells comprising DNA of step (a) with a hypertonic, high salt reagent having a concentration of salt therein so as to form a suspension of said biological cells;
   (c) contacting the suspension of step (b) with a lysis reagent so as to lyse the biological material containing DNA to form a lysate comprising DNA and non-DNA biological components of the biological material, wherein the hypertonic, high salt reagent in step (b) comprises salt in an amount effective to precipitate proteins out of the lysate; and
   (d) separating the DNA from the non-DNA biological components of the lysate of step (c) to yield isolated DNA.

2. The method of claim 1, wherein the biological sample is selected from the group consisting of animal tissue, cultured animal cells, blood cells, and body fluids.

3. The method of claim 1, wherein the biological sample is a bone marrow sample.

4. The method of claim 1, wherein the biological sample is whole blood.

5. The method of claim 1, where the non-DNA biological component is selected from the group consisting of proteins, lipids, RNA, and carbohydrates.

6. The method of claim 1, wherein the salt is selected from the group consisting of soluble sodium, ammonium, or potassium salts.

7. The method of claim 1, wherein the concentration of the salt is greater than 1 M.

8. The method of claim 1, wherein the concentration of the salt is greater than 2 M.

9. The method of claim 1, wherein the lysis reagent comprises a detergent.

10. The method of claim 1, wherein the lysis reagent comprises an anionic detergent.

11. The method of claim 10, wherein the anionic detergent is chosen from the group consisting of sodium, potassium, and lithium salts of dodecyl sulfate.

12. The method of claim 10, wherein the concentration of the anionic detergent is greater than 0.1% w/v based on the volume of the lysis reagent.

13. The method of claim 1, wherein the lysis reagent further contains an RNase solution.

14. The method of claim 1, wherein the step of separating the DNA from the lysate further comprises physically precipitating non-DNA biological components from the lysate without the use of any additional reagents, to yield a non-DNA precipitate, and a solution containing DNA.

15. The method of claim 14, wherein the step of separating the DNA from the lysate further comprises centrifuging the lysate.

16. The method of claim 15, further comprising contacting said solution containing DNA with an alcohol to yield a precipitate comprising isolated DNA.

17. The method of claim 16 further comprising contacting the isolated DNA with a wash solution.

18. The method of claim 16, wherein the isolated DNA is treated with a hydration reagent.

19. A method for isolating DNA from a biological sample comprising red blood cells and white blood cells comprising the following sequential steps:
(a) contacting the biological sample with a red blood lysis reagent to lyse the red blood cells;
(b) separating the white blood cells from the lysed red blood cells;
(c) contacting the white blood cells with a hypertonic, high-salt reagent having a concentration of salt therein to suspend the white blood cells in a solution of said hypertonic, high-salt reagent;
(d) subsequently contacting the white blood cells of step (c) with a lysis reagent so as to lyse the biological material containing DNA to form a lysate containing DNA and non-DNA cellular material, wherein the hypertonic, high salt reagent in step (c) comprises salt in an amount effective to precipitate proteins out of the lysate; and
(e) separating the DNA from non-DNA cellular material of the lysate to yield isolated DNA.

20. The method of claim 19, wherein the biological sample is selected from the group consisting of blood cells and body fluids.

21. The method of claim 19, wherein the biological sample is a bone marrow sample.

22. The method of claim 19, wherein the biological sample is whole blood.

23. The method of claim 19, where the non-DNA biological component is selected from the group consisting of proteins, lipids, RNA, and carbohydrates.

24. The method of claim 19, wherein the salt is selected from the group consisting of soluble sodium, ammonium, or potassium salts.

25. The method of claim 19, wherein the concentration of the salt is greater than 1 M.

26. The method of claim 19, wherein the concentration of the salt is greater than 2 M.

27. The method of claim 19, wherein the lysis reagent comprises a detergent.

28. The method of claim 19, wherein the lysis reagent comprises an anionic detergent.

29. The method of claim 28, wherein the anionic detergent is chosen from the group consisting of sodium, potassium, and lithium salts of dodecyl sulfate.

30. The method of claim 28, wherein the concentration of the anionic detergent is greater than 0.1% w/v based on the volume of the lysis reagent.

31. The method of claim 19, wherein the lysis reagent further contains an RNase solution.

32. The method of claim 19, wherein the step of separating the DNA from the lysate further comprises physically precipitating non-DNA biological components from the lysate without the use of any additional reagents, to yield a non-DNA precipitate, and a solution containing DNA.

33. The method of claim 32, wherein the step of separating the DNA from the lysate further comprises centrifuging the lysate.

34. The method of claim 32, further comprising contacting said solution containing DNA with an alcohol to yield a precipitate comprising isolated DNA.

35. The method of claim 34 further comprising contacting the isolated DNA with a wash solution.

36. The method of claim 34, wherein the isolated DNA is treated with a hydration reagent.

37. A method for isolating DNA from a biological sample comprising microbial cells comprising the following sequential steps:
(a) separating the cells comprising DNA from the remainder of the biological sample;
(b) contacting the separated cells comprising DNA of step (a) with a hypertonic, high salt reagent having a concentration of salt therein so as to form a suspension of said biological cells;
(c) contacting the suspension of step (b) with a lysis reagent so as to lyse the biological material containing DNA to form a lysate comprising DNA and non-DNA biological components of the biological material, wherein the hypertonic, high salt reagent in step (b) comprises salt in an amount effective to precipitate proteins out of the lysate; and
(d) separating the DNA from the non-DNA biological components of the lysate of step (c) to yield isolated DNA.

38. The method of claim 37, wherein said microbial cells are bacterial cells.

* * * * *